United States Patent
Bayat

(10) Patent No.: US 7,540,873 B2
(45) Date of Patent: Jun. 2, 2009

(54) FOUR FUNCTION MICROSURGERY INSTRUMENT

(75) Inventor: Ardeshir Bayat, Manchester (GB)

(73) Assignee: Inasurgica, LLC., Los Angeles, CA (US)

(*) Notice: Subject to any disclaimer, the term of this patent is extended or adjusted under 35 U.S.C. 154(b) by 431 days.

(21) Appl. No.: 11/471,067

(22) Filed: Jun. 20, 2006

(65) Prior Publication Data

US 2006/0287651 A1  Dec. 21, 2006

Related U.S. Application Data

(60) Provisional application No. 60/692,479, filed on Jun. 21, 2005.

(51) Int. Cl.
  *A61B 18/18*  (2006.01)
  *A61M 1/00*  (2006.01)
(52) U.S. Cl. .................................. 606/51; 604/153
(58) Field of Classification Search ................. 604/153
  See application file for complete search history.

(56) References Cited

U.S. PATENT DOCUMENTS

| | | | |
|---|---|---|---|
| 4,492,231 A * | 1/1985 | Auth | 606/42 |
| 4,567,890 A | 2/1986 | Ohta et al. | |
| 4,950,281 A | 8/1990 | Kirsch et al. | |
| 5,151,102 A | 9/1992 | Kamiyama et al. | |
| 6,527,745 B1 | 3/2003 | Kanda et al. | |
| 6,926,676 B2 | 8/2005 | Turturro et al. | |

FOREIGN PATENT DOCUMENTS

GB  2367751 A * 4/2002

OTHER PUBLICATIONS

Bayat, A., A Novel, Triple-Function Vessel Dilator, Plastic and Reconstructive Surgery, Jan. 2003, vol. 111(1), pp. 501-502 (American Society of Plastic Surgeons).
Bayat, A. et al., A Novel Irrigating Vessel Dilator For Microsurgery, Plastic and Reconstructive Surgery, Sep. 2001, vol. 108(3), pp. 798-799 (Am. Soc. of Plastic Surg.).

* cited by examiner

*Primary Examiner*—Nicholas D Lucchesi
*Assistant Examiner*—Jason Flick
(74) *Attorney, Agent, or Firm*—Howard L. Hoffenberg, Esq.; The IP Law Offices of Howard L. Hoffenberg, Esq.

(57) ABSTRACT

The present invention is directed to a four function microsurgery instrument performing the functions of aspiration, irrigation, dilation and cauterization. An embodiment of the present invention has a body; a first and second side arms with integral dilation tips having an electrical conducting surface; a power control and transmission system; a common conduit that delivers irrigation-fluid and aspiration-suction in proximity to the dilation tips and an irrigation-fluid and aspiration-suction control and transmission system. The instrument provides the advantages of being small in size, being ergonomical, being all-in-one, eliminating the need for a surgeon-user to fumble around in switching between instruments, reducing time consumption and reducing frustration.

4 Claims, 3 Drawing Sheets

FOUR FUNCTION MICROSURGERY INSTRUMENT

CROSS-REFERENCE TO RELATED APPLICATIONS

I hereby claim the benefit of my earlier filed provisional application (application No. 60/692,479) filed Jun. 21, 2005.

BACKGROUND OF THE INVENTION

1. Field of the Invention

This invention is in the field of surgical instruments and more particularly in the field of vessel dilators.

2. Related Art

A vessel dilator provides intra-luminal vessel dilation during surgery. Vessel dilators are frequently used during surgical procedures as aid in fine dissection and vessel anastomosis. As a vessel dilator is inserted into a vessel, the dilator helps to hold the vessel wall and avoid suturing the back to the front wall of the vessel. A conventional vessel dilator comprises a modified forceps having elongated parallel tips which are highly polished. The parallel tips are pressed together to provide a single tapered shaft. The tapered shaft is inserted into a vessel, and the parallel tips are allowed to separate thereby dilating the vessel.

Often, when a vessel is to be sutured, the vessel must be irrigated using an irrigator. Irrigation is used to prevent drying of tissue, to remove tissue debris and blood, to keep vessel ends open and prevent floating adventitia at vessel ends interrupting satisfactory microvascular suturing and anastomosis. Irrigation keeps the operative field clean, and inhibits blood clotting inside the lumen of the blood vessel.

Suction keep the operative field clean and inhibit blood clotting inside the lumen of the blood vessel.

Anastomosis covers a variety of procedures in which blood vessels (or other tubular members) are joined or reconnected. Vessels may be joined in a variety of relative orientations, including end-to-side, and end-to-end. Anastomosis is traditionally performed by suturing the vessels together at the juncture between them. Alternatives to suturing have been developed, in order to prevent thrombosis which tends to occur at the points of penetration of the sutures. One such alternative, particularly for larger vessels, involves mechanical connectors such as collars. A second alternative is the use of surgical clips which are applied along the vessel juncture to perform a holding function similar to that of sutures, without penetrating the vessel walls.

Cauterization seals vessels and arrest bleeding. A conventional bipolar-type blood vessel coagulation/stanching device uses high-frequency current. A number of such conventional devices employing a spark gap method generating high frequency ranging between 0.5 to 3 MHz have been used. The two electrodes (active and inactive electrodes) of the bipolar type device are provided at both ends of a pair of forceps to be held by hand. Electric current flows only through the living tissue held between the ends of the forceps. Since electric damage to a patient is applied only to a limited portion to be coagulated, bleeding from a blood vessel can be stopped completely without injuring other tissues. More specifically, the stanching effect of the device is obtained by coagulating the blood vessel using localized heating caused by the high-frequency current flowing through the living tissue.

The surgeon must alternate among dilation, irrigation, suction during vessel dissection and anastomosis and cauterization, using separate dilation, suction, irrigation and cauterization instruments. The act of switching among these four instruments is time-consuming and can interrupt the surgeon's attention and concentration.

Applicant herein has invented a three functional vessel dilator performing the functions of dilation, irrigation, suction during vessel dissection and anastomosis. Still, when suturing a blood vessel or otherwise performing operative tasks, a surgeon must alternate between three functional vessel dilator and a cauterization instrument. Alternating between these instruments is time consuming, and interrupts the surgeon's attention.

There is a need for a four function vessel dilator performing the functions of dilation, irrigation, suction during vessel dissection and anastomosis and cauterization. A simple to use, easy to handle, lightweight, atraumatic, all-in-one instrument can significantly reduce operative time and improve the overall efficiency of the operative procedure. The advantage of a totally disposable instrument is also evident in its low cost and the avoidance of transmission of pathogenic agents, because current sterilization techniques are not totally fail-safe.

The present invention satisfies these needs, as well as others, and generally overcomes the presently known deficiencies in the art.

SUMMARY OF THE INVENTION

The present invention is directed to a four function microsurgery instrument 10 performing the functions of aspiration, irrigation, dilation and cauterization. An embodiment of the present invention has a body; a first and second side arms with integral dilation tips having an electrical conducting surface; a power control and transmission system; a common conduit that delivers irrigation-fluid and aspiration-suction in proximity to the dilation tips and an irrigation-fluid and aspiration-suction control and transmission system. Other embodiments containing some or all of the foregoing elements, as well as other elements, fall within the scope of this invention. The present invention has many advantages which include an microinstrument configured so all the functions fit together in one instrument and enabling a user surgeon to perform operative tasks without having to switch instruments.

BRIEF DESCRIPTION OF THE DRAWINGS

These and other features, aspects and advantages of the present invention will become better understood with reference to the following description, appended claims and accompanying drawings where:

DETAILED DESCRIPTION OF THE INVENTION

The invention is a four function microsurgery instrument 10 performing the functions of aspiration, irrigation, dilation and cauterization. The device is a micro-instrument designed for work with vessels having a diameter of on or about one or two millimeters.

Figure 1:
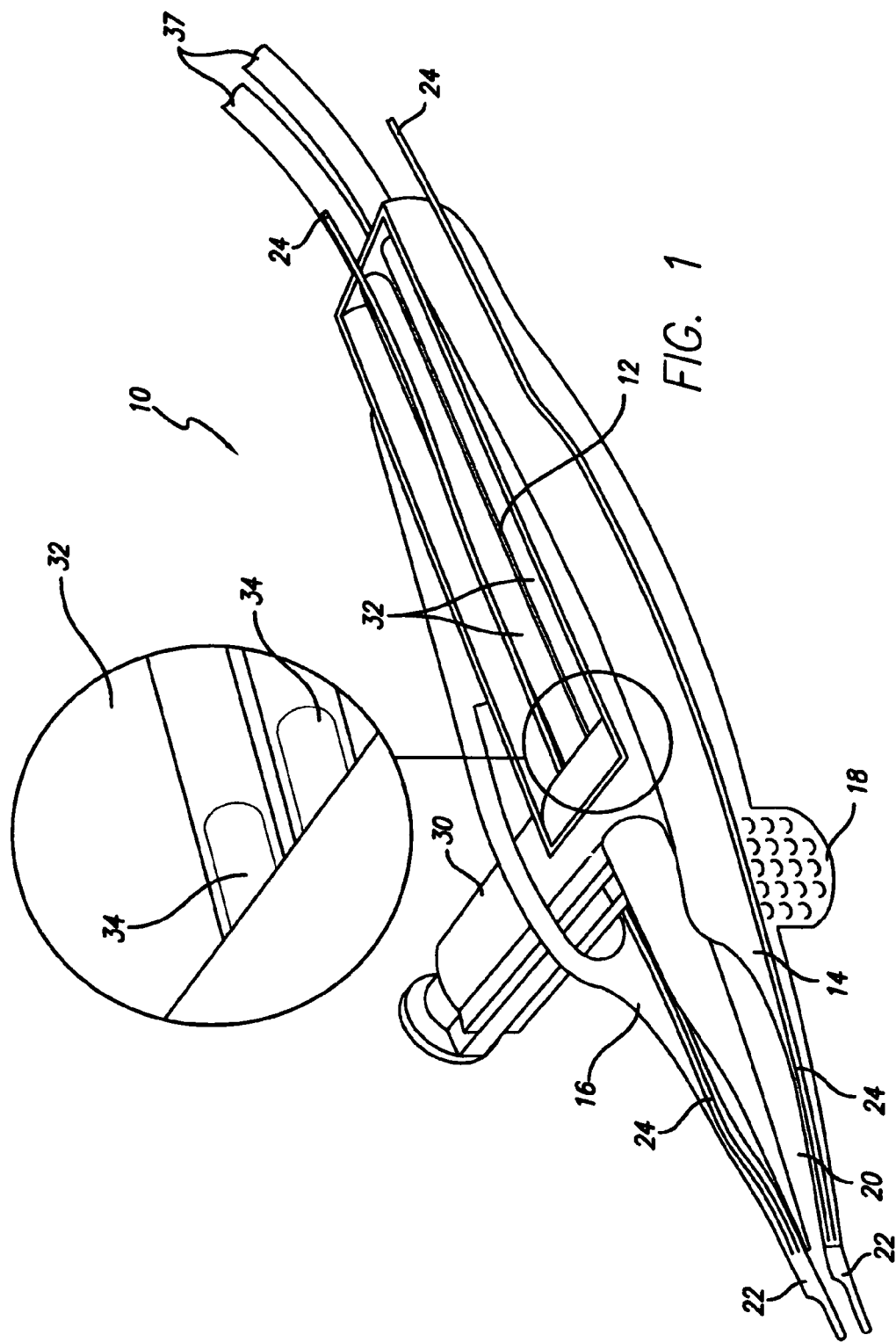
FIG. 1 which is a perspective view of the invention looking across a side with a top lid portion removed and showing internal tubing, along with a blowup insert featuring tubing inserted on tube ports.

Referring to FIG. 1, an embodiment of the four function microsurgery instrument 10 has a body 12. The body 12 is dimensioned to be held in user's palm having front, back, side, top and bottom regions. The body 12 is typically and preferably made of plastic and most preferably a polycarbonate. Preferably, the body 12 is palm sized and ergonomically shaped to fit within a palm.

Continuing to refer to FIG. 1, there are a pair of opposing side arms 14, 16 (referred to as a first side arm 14 and a second side arm 16) that extend from the front region of the body 12 in a direction away from the front region. The opposing side arms 14, 16 extend in substantially parallel fashion. These side arms 14, 16 have a shaft like configuration. Typically, the side arms 14, 16 taper gradually to a narrow breadth as distance increases from the body 12.

Preferably, the outer surfaces of the side arms 14, 16 (that is the surface that does not oppose the other side arm) are provided with undulations which facilitate gripping of the side arms 14, 16. Most preferably, there can be a thumb/finger tab 18 to enhance ergonomics. This thumb/finger tab 18 obtrusively projects from a side arm and is positioned to enhance gripping, control and the ergonomics of the instruments. The thumb/finger tab 18 can further have an array recesses and protrusions/nodulations to further enhance gripping.

The side arms 14, 16 are fabricated from a resilient and insulative material. Preferably, the side arms 14, 16 are made of plastic; more preferably, they are made from a polycarbonate and most preferably, the side arms 14, 16 are the same material as the body 12.

Each side arm is joined to the body 12 at the front region of the body 12 such that the side arms 14, 16 are resiliently held apart from one another, but may be squeezed or pressed together. Accordingly, the ends of the first and second side arms 14, 16, referred to as dilation tips 22 and discussed below, are in a spaced apart relationship with a gap there between. A user can squeeze and release the side arms 14, 16 to adjust the size of this gap.

Preferably, the side arms 14, 16 can be squeezed so as to bring together the dilation tips 22 at the ends of the side arms 14, 16. In one embodiment, the side arms 14, 16 are spaced apart a sufficient distance on the front region of the body 12 so that the common conduit (discussed below) does not interfere with the closure of the side arms 14, 16 as the dilator tips are brought together.

In another embodiment, there is a groove (not illustrated) in the inner surface of the first side arm 14 (that is, the surface that opposes the second side arm 16). The common conduit 20 is received in this groove in the inner surface of the first side arm 14. The groove is dimensioned such that the common conduit 20 totally fits within it. In the alternative, the groove is dimensioned so that the common conduit 20 partially fits into the first side arm 14 and there is a groove in the inner surface of the second side arm 16 that mates with the common conduit 20 in the first side arm 14. Thus with the side arms 14, 16 are pressed together, this groove in the second side arm 16 allows the dilation tips of the side arms 14, 16 to close with perfect approximation.

Continuing to refer to FIG. 1, the side arms 14, 16 each terminate in a dilation tip 22. The dilation tip 22 is configured for contacting a blood vessel and is approximately shaped like "b" rotated 90 degrees. The dilation tips 22 are typically unitary with the side arms 14, 16. The dilation tip 22 has an electrical conducting surface. The electrical conducting surface is made out of metal or conducting polymer/resin. Suitable metals include steel and titanium. A preferred material is a metal and a most preferred material is steel.

Figure 2:
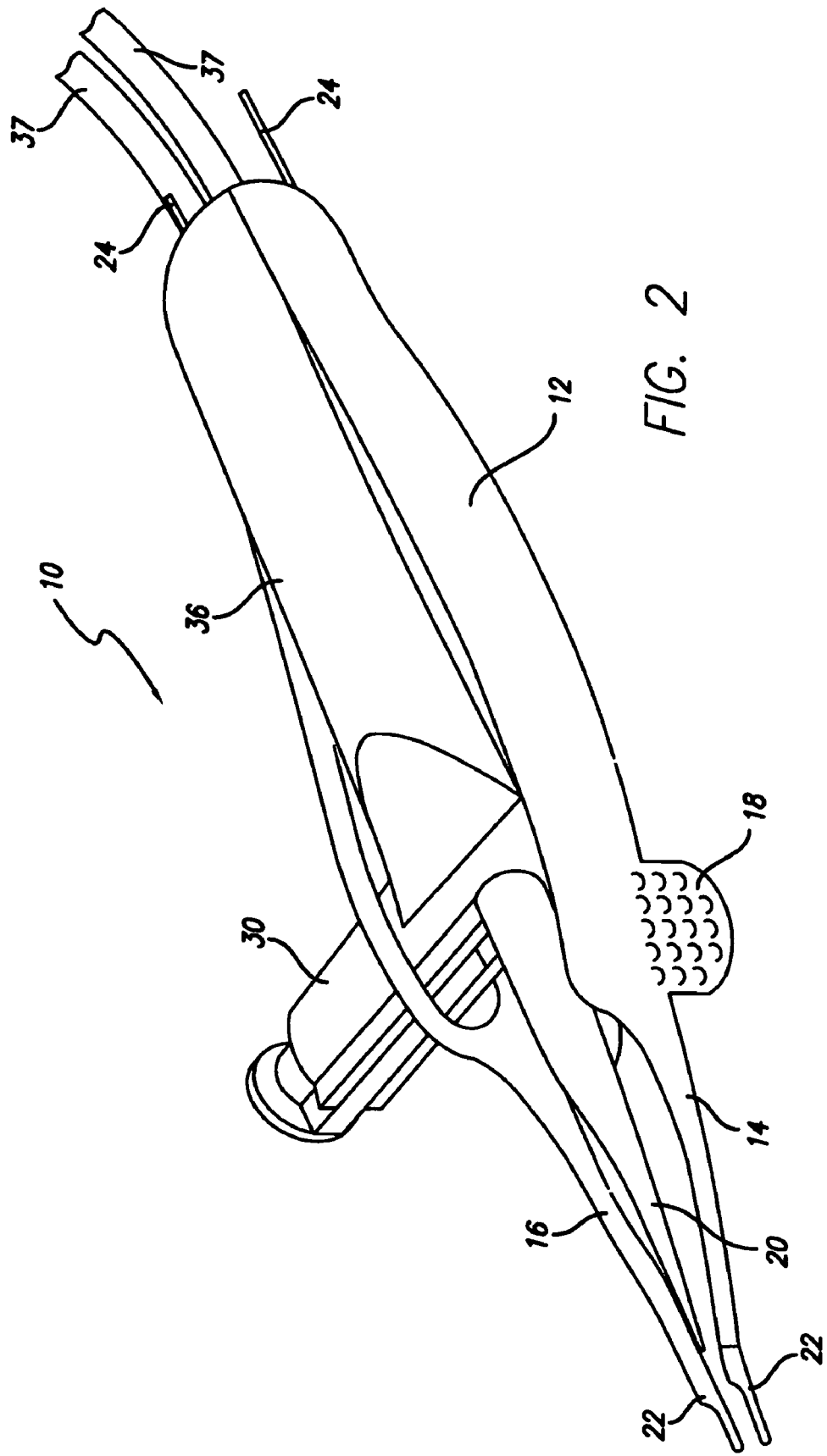
FIG. 2 which is a perspective view of the four function microsurgery instrument according to the present invention looking from the top and down and FIG. 3 which is a hybrid perspective and schematic view of the four function microsurgery instrument according to the present invention looking from the top and down with the foot pedal switch shown in schematic format.
Figure 3:
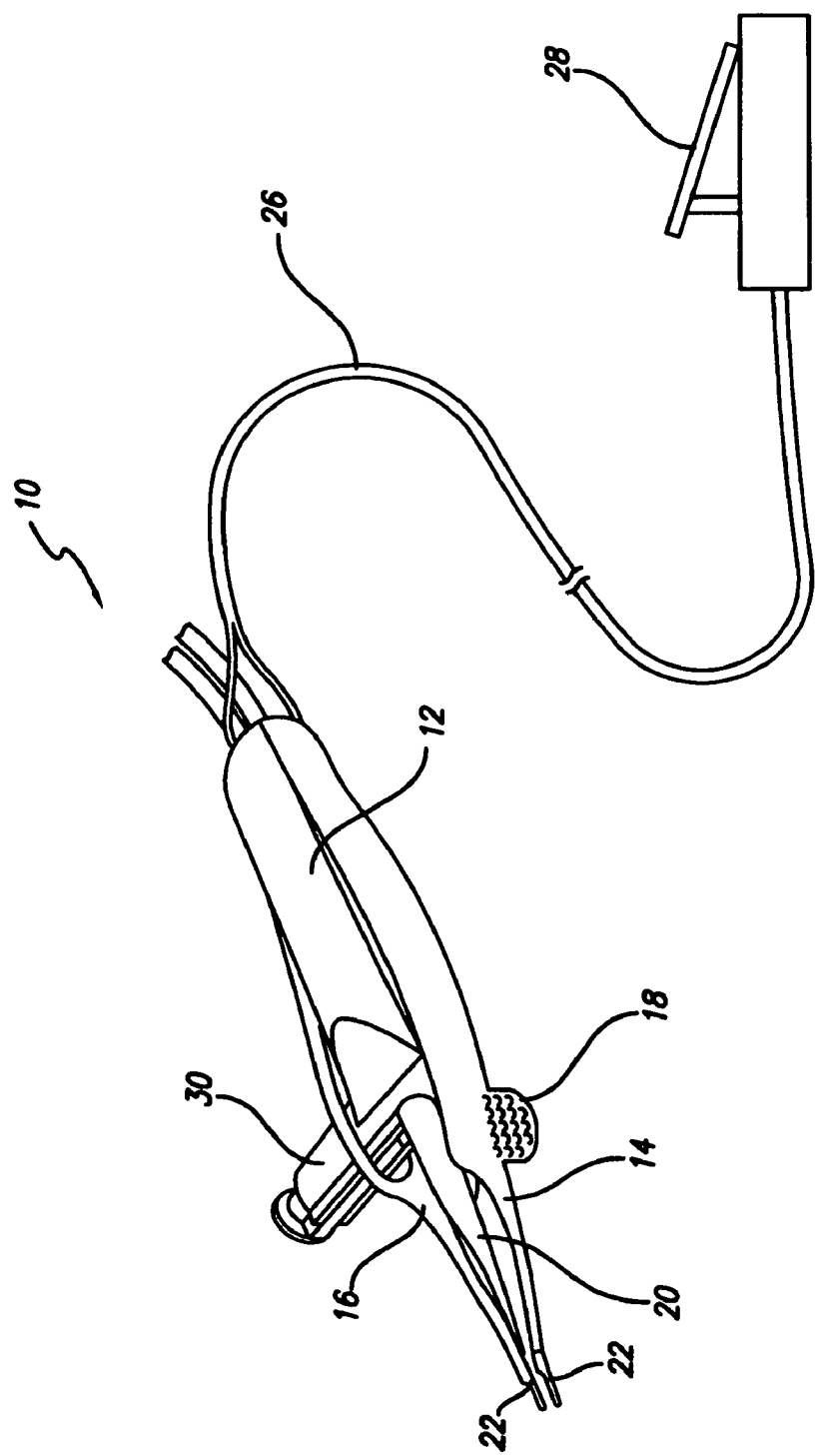

Referring to FIG. 2, each side arm 14, 16 contains an elongated electrical conductor 24. The elongated electrical conductor 24 originates at the dilation tip 22 and is in electrical communication with the conducting surface of the dilation tip 22. The elongated electrical conductor 24 runs laterally through the side arm. Each elongated electrical conductor 24 in each side arm is in electrical communication with a power cable means. The power cable means includes a portion that runs through the body 12 and a portion that extends from the body 12 in a direction away from the back region. Optionally, the power cable means 26 can include at the back region of the body 12 a connector to provide a junction for attachment and release of an electrical power cable means 26. Thus an electric circuit is creatable from an electric power source so that electric power is supplied for bipolar cauterization at the dilation tips 22.

There is power control means 28 for manually actuating the supply of electric power for bipolar cauterization at the dilation tips 22. This power control means 28 along with the power transmission means comprise a power control and transmission system. In one embodiment of the present invention, the power control means 28 is a foot pedal switch 28 in electrical communication with the power transmission system whereby electric power from a power source is turned on so as to be supplied for bipolar cauterization at the dilation tips 22.

In another embodiment of the present invention, the power control means 28 is momentary contact switch (touch surface or a pole) (not illustrated) which is in intermittent electrical communication between an elongated conductor in a side arm and the power transmission means. The power transmission means provides electric power from a power source which manually actuated by this switch so as to supply power for bipolar cauterization at the dilation tips 22.

Referring to FIG. 1, a common conduit 20 extends from the body 12 in a direction away from the front region and delivers irrigation-fluid and aspiration-suction in proximity to the dilation tips 22. The term common conduit 20 includes two separate conduits, co-axial conduits with two channels and side-by-side conduit strips where there are two conduits/channels with one delivering fluid and the other suction. Typically and preferably, the common conduit 20 is a single channel/conduit that is used to provide irrigating fluid, or alternatively the common conduit 20 can be used to extract fluid. The function provided by the common conduit 20 is determined by an irrigation-fluid and aspiration-suction control and transmission system.

The common conduit 20 is typically positioned between the opposing arms. It can also be positioned to run along or inside a side arm with a suitable exit port fixture to direct the flow of irrigation-fluid and aspiration suction (not illustrated.) The common conduit 20 can be positioned outside the pair side arms 14, 16 with a suitable exit port fixture to direct the flow of irrigation-fluid and aspiration suction. Preferably, the common conduit 20 is centrally located between the side arms 14, 16 such that when the side arms 14, 16 are pressed together, the common conduit 20 is located immediately behind the dilation tips 22 of the side arms 14, 16.

Typically, the common conduit 20 is a removable plastic needle or cannula 20. The plastics needle is a standard mini Yankauer, which is conventionally used as a cannula 20 in paediatric, anaesthetic and theatres. The needle/cannula 20 is attached to a central spar (common conduit port (not illustrated)) which extends from the front region of the body 12. The needle/cannlula is pushed onto the common conduit port (not illustrated). Friction between the needle/cannula 20 and the common conduit port (not illustrated) is sufficient to hold the needle/cannula 20 in place.

There is an irrigation-fluid and aspiration-suction control and transmission system that is in fluid communication with the common conduit 20 and sources for fluid and vacuum. This system is comprised of a fluid control means 30 and a transmission means.

Referring to FIG. 1, one embodiment of the fluid control means 30 is a plunger valve 30 (discussed further below) extending from the body 12 in a direction away from a side region and positioned for actuation by a user for control of both irrigation-fluid and aspiration-suction control. This plunger valve 30 is in intermittent fluid communication with the common conduit 20 and the fluid communication means 32, 37 (discussed further below.) The term plunger includes valve 30 with a solenoid or other electrical assist that may be actuated by a switch and in particular a momentary contact switch. The term plunger valve (30) includes other forms of valves that have a lever, pole or other feature suitable for manual actuation by a user surgeon. The fluid communication means 32, 37 is in fluid communication with fluid and vacuum sources. Preferably there is a single shaft moveable valve 30 where one pump actuates vacuum and two pumps actuates irrigation fluid or vice versa.

Another embodiment (not illustrated) of the irrigation-fluid and aspiration-suction control system is comprised of a first plunger valve 30 extending from the body 12 in a direction away from a side region and positioned for actuation by a user for control of irrigation-fluid and a second plunger valve (not illustrated) extending from the body 12 in a direction away from a side region and positioned for actuation by a user for control of aspiration-suction. Each plunger valve 30 is in intermittent fluid communication between the common conduit 20 and the fluid communication means 32. The fluid communication means 32 is in fluid communication with fluid and vacuum sources.

The plunger valve 30 is comprised of a central chamber defined by a cylindrical housing, the chamber being connected to the two tube ports and a further port on an opposite side of the chamber (this port is and had been referred to as the common conduit port (not illustrated)). A valve stopper comprises a lower stopping region, a middle cut away region and an upper stopping region. O-rings or molded seals are provided in recesses of the stopping region and are arranged to ensure that a seal is maintained between the stopping regions and the chamber defined by the cylinder.

The operation of the plunger valve 30 is as follows. In a first uppermost position, the lower stopping region is located between the tube ports 34 and the common conduit port (not illustrated). No fluid is allowed to flow to or from the plunger valve 30. In a second middle position, the open region of the stopper is located between the upper tube port 24 and the common conduit port (not illustrated), thereby providing suction to the common conduit 20 (needle/cannula 20) via one of the plastic tubes 32. The lower stopper region is located between the lower tube port 34 and the common conduit port (not illustrated) extending out of the front region of the body 12, thereby preventing the flow of fluid via the lower tube port 34. In a third lowermost position the open region is located between the lower tube port 34 and the common conduit port (not illustrated), thereby allowing fluid to flow from one of the plastics tube 32 to the common conduit 20 (needle/cannula.) The upper stopping region is located between the upper port 34 and the common conduit port (not illustrated), thereby preventing suction from common conduit 20 (needle/cannula) via one of the plastics tubes.32

A helical spring is located in the base of the cylinder and biases the stopper to the first uppermost position in which both inlet ports are closed. The stopper is provided with a hook which engages a recess provided in the exterior of the cylinder. The hook and the recess combine to limit the movement of the stopper to a predetermined range of motion. In particular, the hook and recess prevent the stopper from inadvertently being removed from the cylinder.

Referring to FIG. 2, a fluid communication means 32 is configured as follows. A pair of tubes 32 runs through the body 12. One tube 32 provides vacuum and the other tube provides a irrigation fluid 32. At the rear of the body 12 there can be connectors (not illustrated) for the tubing 32 for attachment to a vacuum and irrigation fluid source (not illustrated.) The connector can be a standard luer lock (not illustrated) (a known apparatus conventionally used to connect a needle to an intravenous set) which is attached onto the rear end of the body 12. Optionally, the body 12 can have a lid 36 on the top or side of the body 12 with connectors for the tubing (ports) 34 being within the body 12. When the lid 36 is open, tubing 32 can be attached to or released from the connectors (ports) 34.

In an embodiment of the four function microsurgery instrument 10, a luer lock (not illustrated) on the rear region of the body is connected to an appropriately sized connecting tube 32 (an intravenous set), which is in turn can be attached to a 50 milliliter syringe containing heparin/saline. Variation of pressure applied to the syringe will produce a corresponding variation of the rate of fluid flow from the common conduit 20. The rate of fluid flow from the conduit can thus be altered at the request of a user (surgeon.) The four function microsurgery instrument 10 may be connected to more than one syringe through a multi-channel connector. Where more than one syringe is provided, it is possible for more than one assistant to assist with irrigating. The length of the connecting tube can be selected depending upon how close or far away a surgical assistant is situated from a surgeon. Commercially available dispensable intravenous sets of different lengths may be used.

In an alternative embodiment, the fluid may be delivered to the four function microsurgery instrument 10 under pressure using an automated pump. The four function microsurgery instrument 10 may then include a valve 30 which is used by the surgeon to control the rate of flow of fluid from the four function microsurgery instrument 10. The valve 30 is suitably provided on the first side arm 14.

In an alternative embodiment, the four function microsurgery instrument 10 is in a modular configuration so that the instrument can be disassembled for easy cleaning and reassembled. Preferably, there is one module comprised of the side arms 14, 16 with a harness or docking apparatus to receive a central unit contain the other components of the instrument as previously described.

Regarding alternative best modes for carrying out this invention, preferably, the dilator tip 20 of the tapered shaft side arm 14, 16 has a diameter of less than 5 millimeters. Preferably, the dilation tip 22 of the tapered shaft side arm 14, 16 has a diameter of 3 millimeters or less. Preferably, the side arms 14, 16 are provided with gripping means such as a thumb/finger tab 18. Preferably, the thumb/finger tab gripping means 18 comprises a recess provided with a series of protrusions. Preferably, the connection between the side arms 14, 16 and body 12 is resilient.

Regarding alternative best modes for carrying out this invention, preferably, the common conduit 20 is arranged to deliver irrigating fluid or suction to a dilator tip 20 of the side arm 14, 16. Preferably, the common conduit 20 extends between the side arms 14, 16 of the four function microsurgery instrument 10. Preferably, the common conduit 20 is fabricated from plastics. Preferably, a groove is provided in an opposing side arm 14, 16, the groove being dimensioned to receive the common conduit 20 when the side arms 14, 16 are held together and preferably, a common conduit 20 is fixed to one of the side arms 14, 16. Preferably, the common conduit 20 is connected to a luer lock or common conduit port (not illustrated) extending out from the front region of the body 12. Preferably, the common conduit 20 is a 24 gauge needle/cannula.

Regarding alternative best modes for carrying out this invention, preferably, the four function microsurgery instrument 10 is provided with a valve 30 moveable between an irrigating position in which irrigating fluid passes through the plunger valve 30, a suction position in which air and extracted fluid passes through the plunger valve 30, and an off position in which the plunger valve 30 is shut. Preferably, the plunger valve 30 is provided with cylindrical ports 34, each cylindrical port 34 being dimensioned to allow a tube 32 to be pushed onto the port such that the tube 32 is fixed to the port 34 by friction between the tube 32 and the port 34. Preferably, the plunger valve 30 comprises a moveable stopper which in the irrigating position provides a connection between the first tube and the common conduit 20, in the suction position provides a connection between the second tube and the common conduit 20, and in the off position provides no connection between the common conduit 20 and the first tube or the second tube. Preferably, the moveable stopper is resiliently biased towards the off position. Preferably, the moveable stopper is provided with a catch which prevents the stopper from inadvertently becoming detached from the four function microsurgery instrument 10.

Regarding alternative best modes for carrying out this invention, preferably, two tubes 32 are connected to the plunger valve 30, a first tube 32 carrying irrigating fluid, and a second tube 32 delivering suction. Preferably, the luer lock (not illustrated) is connected via flexible tubing 32 to one or more reservoirs (not illustrated) containing irrigating fluid. Preferably, the one or more reservoirs are syringes. Preferably, irrigating fluid is delivered to the four function microsurgery instrument 10 using an automated pump.

Regarding alternative best modes for carrying out this invention, preferably, the four function microsurgery instrument 10 may be dismantled into its constituent parts to facilitate sterilization.

The four function microsurgery instrument 10 is suitable for microsurgical operations in the fields of: plastic and reconstructive surgery, hand surgery, head and neck surgery, otolaryngology, obstetrics and gynecology, oral and maxillofacial surgery, neurosurgery, dental surgery, opthalmology, cardiothoracic surgery, pediatric surgery and urology. A larger dimensioned four function microsurgery instrument 10 is suitable for use in other types of surgery such as general surgery, vascular surgery, spinal surgery, orthopaedic surgery, and breast surgery.

The instrument provides the advantages of size, being a microinstrument, and four cooperating functions.

EXAMPLES

The following example further describe and demonstrate embodiments within the scope of the present invention. The examples are given solely for the purpose of illustration and are not to be construed as limitations or restrictions of the present invention, as persons skilled in the art will quickly realize many variations thereof are possible that are all within the spirit and scope of the invention.

The four function microsurgery instrument 10 is approximately 11 centimeters in length. An angulation of each dilation tip 22 of 10 degrees, a tip diameter 3 millimeters and common conduit needle 20 that is a 24 gauge needle.

Although the present invention has been described in considerable detail with reference to certain preferred versions thereof, other versions are possible with substituted, varied and/or modified materials and steps are employed. These other versions do not depart from the invention. Therefore, the spirit and scope of the appended claims should not be limited to the description of the preferred versions contained herein.

What is claimed is:

1. A four function microsurgery instrument for vessel dilation, irrigation, aspiration and cauterization comprised of:
   a) a body that is dimensioned to be held in user's palm having front, back, side, top and bottom regions;
   b) a first and second side arm for which each:
      i) extends from the body in a direction away from the front region and is oppositely opposed to the other side arm;
      ii) is fabricated from a resilient and insulative material and contains an elongated electrical conductor that runs laterally through the sidearm and
      iii) terminates in a dilation tip that has an electrical conducting surface which is in electrical communication with the elongated electrical conductor,
      such that the dilation tips of the first and second side arms are in a spaced apart relationship with a gap there between and a user can squeeze and release the side arms to adjust the size of this gap;
   c) a power control and transmission system comprised of a power cable means that is in electrical communication with the elongated conductors of the first and second side arms and extends from the body in a direction away from the back region to a foot pedal switch whereby electric power is supplied for bipolar cauterization at the dilation tips;
   d) a common conduit extending from the body in a direction away from the front region that delivers irrigation-fluid and aspiration-suction in proximity to the dilation tips
   e) an irrigation-fluid and aspiration-suction control and transmission system comprised of
      (i) a plunger valve extending from the body in a direction away from a first side arm in a plane that passes through the two side arms, positioned for actuation by a user and that is in fluid communication with the common conduit and
      (ii) a fluid communication means that is in fluid communication with the plunger valve and extends from the body in a direction away from the back region whereby irrigation-fluid and aspiration-suction are supplied and
   f) a thumb/finger tab obtrusively projecting from a second side arm and positioned to enhance ergonomics when actuating the plunger valve.

2. The four function microsurgery instrument of claim 1 where the side arms and dilation tips are fabricated from a plastic material and the dilation tips have an electrical conducting surface fabricated from metal.

3. A four function microsurgery instrument for vessel dilation, irrigation, aspiration and cauterization comprised of:
   a) a body that is dimensioned to be held in user's palm having front, back, side, top and bottom regions;

b) a first and second side arm for which each:
  i) extends from the body in a direction away from the front region and is oppositely opposed to the other side arm;
  ii) is fabricated from a resilient and insulative material and contains an elongated electrical conductor that runs laterally through the sidearm and
  iii) terminates in a dilation tip that has an electrical conducting surface which is in electrical communication with the elongated electrical conductor,
  such that the dilation tips of the first and second side arms are in a spaced apart relationship with a gap there between and a user can squeeze and release the side arms to adjust the size of this gap;
c) a power control and transmission system comprised of a plunger momentary contact switch extending from the body in a direction away from a side region and positioned for actuation by a user that is in electrical communication with the elongated conductor of the first side arms and a power cable means that is in electrical communication with momentary contact switch and the elongated conductor of the second side arm and extends from the body in a direction away from the back region whereby electric power is supplied for bipolar cauterization at the dilation tips;
d) a common conduit extending from the body in a direction away from the front region that delivers irrigation-fluid and aspiration-suction in proximity to the dilation tips and
e) an irrigation-fluid and aspiration-suction control and transmission system comprised of
  a plunger valve extending from the body in a direction away from a first side arm in a plane that passes through the two side arms, positioned for actuation by a user and that is in fluid communication with the common conduit and
  (ii) a fluid communication means that is in fluid communication with the plunger valve and extends from the body in a direction away from the back region whereby irrigation-fluid and aspiration-suction are supplied and
f) a thumb/finger tab obtrusively projecting from a second side arm and positioned to enhance ergonomics when actuating the plunger valve.

4. The four function microsurgery instrument of claim 3 where the side arm and dilation tip are fabricated from a plastic material and the dilation tip has an electrical conducting surface fabricated from metal.

* * * * *